United States Patent
Glozman et al.

(10) Patent No.: US 10,561,823 B2
(45) Date of Patent: Feb. 18, 2020

(54) INFLATABLE CHAMBER DEVICE FOR MOTION THROUGH A PASSAGE

(71) Applicant: Technion Research and Development Foundation Ltd., Haifa (IL)

(72) Inventors: Daniel Glozman, Kfar Adummim (IL); Noam Hassidov, Bustan Hagalil (IL); Moshe Shoham, Hoshaya (IL)

(73) Assignee: TECHNION RESEARCH & DEVELOPMENT FOUNDATION LTD., Haifa (IL)

( * ) Notice: Subject to any disclaimer, the term of this patent is extended or adjusted under 35 U.S.C. 154(b) by 460 days.

(21) Appl. No.: 15/218,025

(22) Filed: Jul. 24, 2016

(65) Prior Publication Data

US 2016/0346514 A1    Dec. 1, 2016

Related U.S. Application Data

(63) Continuation of application No. 12/526,271, filed as application No. PCT/IL2008/000173 on Feb. 10, 2008, now Pat. No. 9,427,143.
(Continued)

(51) Int. Cl.
*A61B 1/00* (2006.01)
*A61M 25/01* (2006.01)
(Continued)

(52) U.S. Cl.
CPC ..... *A61M 25/0155* (2013.01); *A61B 1/00082* (2013.01); *A61B 1/00156* (2013.01);
(Continued)

(58) Field of Classification Search
CPC .................................................. A61B 1/00156
(Continued)

(56) References Cited

U.S. PATENT DOCUMENTS

| 4,176,662 A | 4/1979 | Frazer |
| 5,090,259 A | 2/1992 | Shishido et al. |

(Continued)

FOREIGN PATENT DOCUMENTS

| DE | 3425483 A1 | 1/1986 |
| EP | 0540858 A1 | 5/1993 |
| WO | 2007/017876 | 2/2007 |

OTHER PUBLICATIONS

M. Johnson: "The Mullins effect in equibiaxial extension and its influence on the inflation of a balloon," International Journal of Engineering Science, vol. 33, No. 2, Jan. 1, 1995, pp. 223-245. (Year: 1995).*

Supplementary European Search Report and Search Opinion in corresponding European Application No. 08710173.9 dated Nov. 23, 2010.
(Continued)

*Primary Examiner* — Alexandra L Newton
*Assistant Examiner* — Rynae Boler
(74) *Attorney, Agent, or Firm* — Daniel Feigelson; Fourth Dimension IP

(57) ABSTRACT

A self-propelled device for locomotion through a lumen, comprising a set of serially arranged inflatable chambers, adjacent chambers being fluidly connected, and a fluid source attached to one end of the set, such that the chambers inflate sequentially. The chambers are constructed of an elastic material and have a wall thickness and dimensions such that they have a characteristic with a non-monotonous relationship between the inflation pressure within the chamber and the chamber's inflated size. The characteristic is such that after an initial inflation pressure peak, the non-monotonous relationship adopts a negative slope, such that the volume of the chamber increases more rapidly than the volume of fluid flowing into it, and the inflation pressure of the chamber falls. This effect causes the chamber to inflate and anchor rapidly, while essentially slowing down the
(Continued)

inflation of the succeeding chamber until inflation of the first is complete.

10 Claims, 7 Drawing Sheets

Related U.S. Application Data

(60) Provisional application No. 60/900,109, filed on Feb. 8, 2007.

(51) Int. Cl.
*A61B 17/12* (2006.01)
*F16L 55/30* (2006.01)
*F16L 55/34* (2006.01)
*F16L 55/36* (2006.01)
*F16L 55/44* (2006.01)
*A61B 1/31* (2006.01)
*A61M 25/10* (2013.01)

(52) U.S. Cl.
CPC .......... *A61B 1/31* (2013.01); *A61B 17/12045* (2013.01); *A61B 17/12136* (2013.01); *A61M 25/0105* (2013.01); *A61M 25/0116* (2013.01); *F16L 55/30* (2013.01); *F16L 55/34* (2013.01); *F16L 55/36* (2013.01); *F16L 55/44* (2013.01); *A61M 25/10* (2013.01); *A61M 2025/1059* (2013.01)

(58) Field of Classification Search
USPC .................................. 600/114–116, 127, 129
See application file for complete search history.

(56) References Cited

U.S. PATENT DOCUMENTS

| | | | |
|---|---|---|---|
| 5,348,538 A * | 9/1994 | Wang | A61M 25/1029 604/103.12 |
| 5,364,353 A | 11/1994 | Corfitsen et al. | |
| 5,500,181 A | 3/1996 | Wang et al. | |
| 5,662,587 A | 9/1997 | Grundfest et al. | |
| 5,987,360 A | 11/1999 | McGrath et al. | |
| 6,007,482 A | 12/1999 | Madni et al. | |
| 6,468,200 B1 * | 10/2002 | Fischi | A61M 1/1072 600/18 |
| 6,702,735 B2 | 3/2004 | Kelly | |
| 6,764,441 B2 | 7/2004 | Chiel et al. | |
| 2003/0125788 A1 | 7/2003 | Long | |
| 2004/0243167 A1 | 12/2004 | Tanaka et al. | |
| 2005/0075662 A1 | 4/2005 | Pedersen et al. | |
| 2005/0197531 A1 * | 9/2005 | Cabiri | A61B 1/00082 600/116 |

OTHER PUBLICATIONS

P.Dario et al, "Development and in vitro testing . . . for computer assisted colonoscopy", Computer Aided Surgery, vol. 4, pp. 1-14, 1999, Wiley.

J. Dietrich et al, "Development of a peristaltically actuated device . . . ", Micro-and Nanostructures of Biological Systems, Halle,Shaker-Verlag,69-88, 2004.

I.Muller et al, "Rubber & Rubber Balloons: Paradigms of Thermodynamics", Lecture Notes. Phys., vol. 637, pp. 7-34 (2004) Springer Verlag, Berlin.

PCT Int'l Search Report and Written Examination of the ISA, dated Sep. 11, 2008 in PCT/IL08/00173.

Office Action dated Sep. 28, 2011 issued by the European Patent Office in corresponding European application No. 08710173.9.

M. Johnson: "The Mullins effect in equibiaxial extension and its influence on the inflation of a balloon," International Journal of Engineering Science, vol. 33, No. 2, Jan. 1, 1995, pp. 223-245.

* cited by examiner

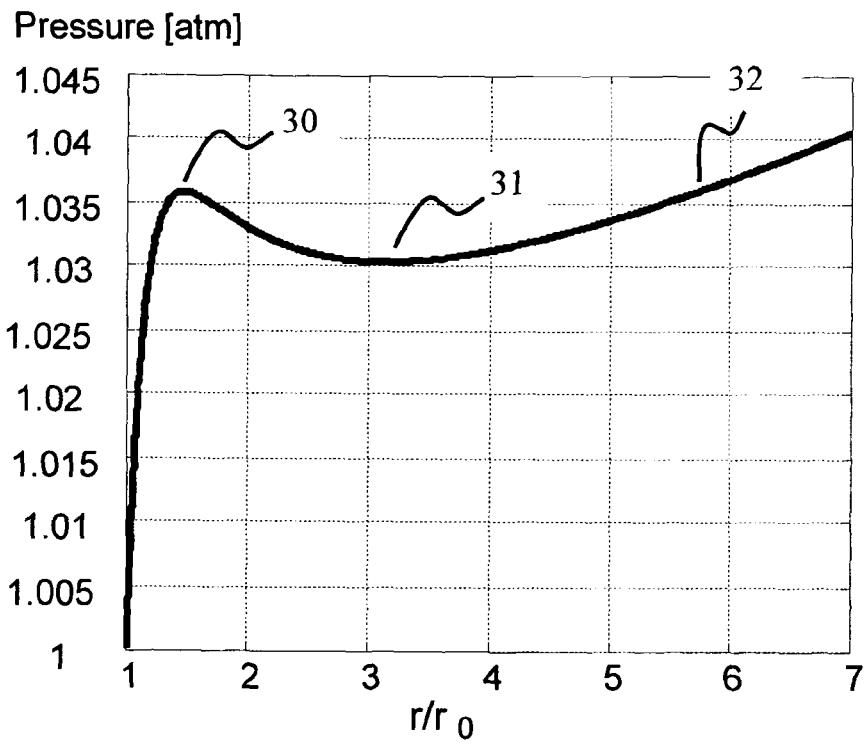
FIG. 3  (s_ = -0.3 bar)
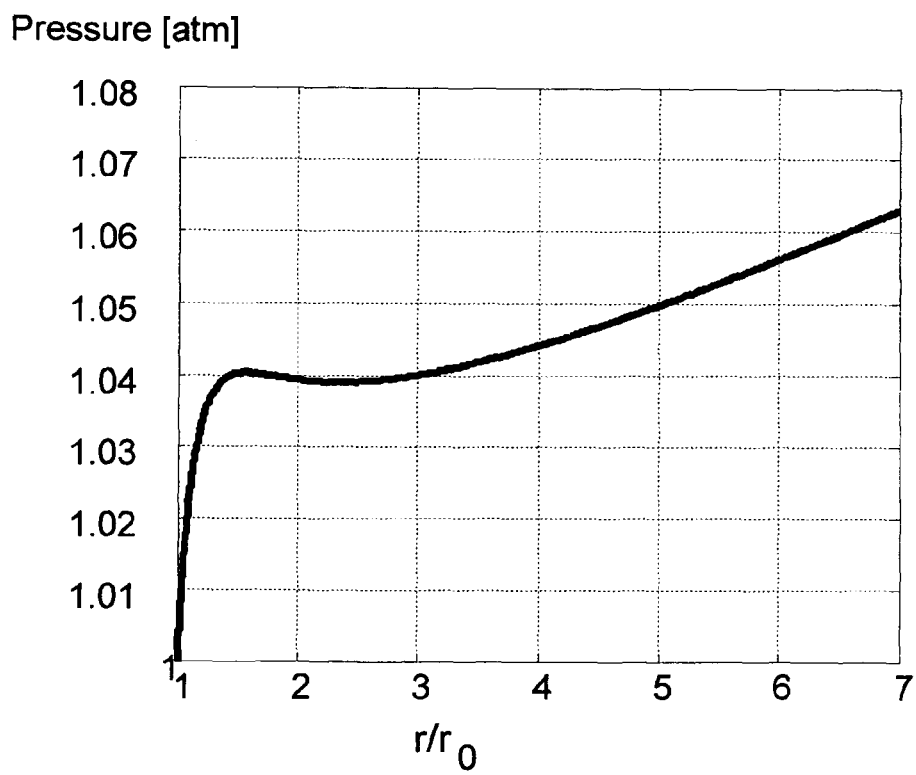
FIG. 4  (s_ = -0.5 bar)

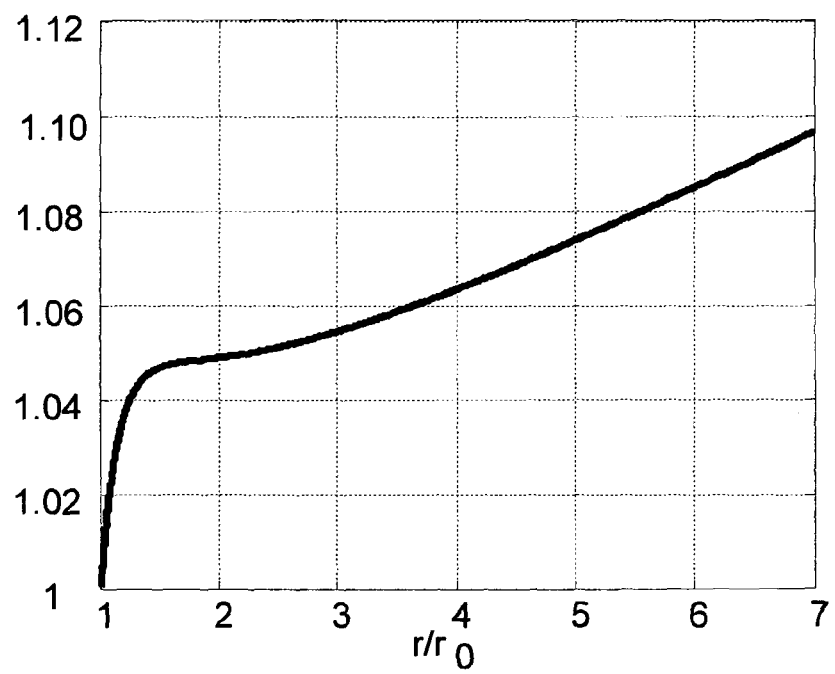
FIG. 5 ($s_- = -0.8$ bar)

INFLATABLE CHAMBER DEVICE FOR MOTION THROUGH A PASSAGE

RELATED APPLICATION INFORMATION

This application is a continuation of U.S. Ser. No. 12/526,271, filed Aug. 7, 2009 as a § 371 application of PCT/IL2008/000173 which was filed Feb. 10, 2008 and claims the benefit of U.S. Ser. No. 60/900,109 which was filed Feb. 8, 2007. The benefit of all of these applications is claimed and their contents are incorporated herein by reference.

FIELD OF THE INVENTION

The present invention relates to the field of inflatable chamber devices capable of self propelled motion through tubes, especially for endoscopic and vascular use.

BACKGROUND OF THE INVENTION

The ability to crawl through long, flexible, and curved tubes has long been a challenge for engineers since numerous applications can benefit from a reliable solution. This ranges from medical applications for treatment and diagnosis to sewer pipes, gas pipes and power plants.

Current solutions often contain a payload such as a camera, which is pushed from the back by a long flexible rod or wire. This is the solution currently used in many medical applications with guide wires or catheters to deliver diagnosis or treatment instruments to the desired position, e.g. in catheterization, colonoscopy, ureteroscopy, dilating balloon, and others.

In some type of applications, it is impossible to push the active head from the back because the force required would cause buckling of the long rod or wire. Additionally, one of the shortcomings of current endoscopes and catheters is that as they are pushed into the passageway manually over a curved path, causing friction, there is a possibility of injury to the inner tissue walls of the passageway.

In search for a solution, a number of locomotion types of propulsion have been developed, which pull at the distal end of the lumen rather then pushing at the proximal end. Examples in non-medical applications include crawling vehicles and spider-like robots. In medical applications, a common solution is that of the inch worm type, that advances by means of peristaltic motion, such as described in the article by P. Dario, et al., "Development and in vitro testing of a miniature robotic system for computer-assisted colonoscopy," published in Computer Aided Surgery, Vol. 4, pp. 1-14, 1999, and in the article by J. Dietrich et al., entitled "Development of a peristaltically actuated device for the minimal invasive surgery with a haptic sensor array" published in Micro- and Nano-structures of Biological Systems, Halle, Shaker-Verlag, 69-88. ISBN 3-8322-2655-9. Such devices are also described, for instance, in U.S. Pat. Nos. 6,764,441, 4,176,662, 5,090,259, 5,662,587, 6,007,482, 5,364,353, and 6,702,735 and also in PCT Application No. PCT/IL2006/000925, to the inventors in the present application.

Most of the above described devices have the disadvantage that a number of control lines or pneumatic tubes are required to operate the device, which complicates both the control system and the physical deployment of the device within the passageway. The device described in the above-mentioned U.S. Pat. No. 5,364,353 for "Apparatus for advancing an object through a body passage" to M.T. Corfitsen et al., and in PCT Application No. PCT/IL2006/000925, for "Tip propelled device for motion through a passage" to M. Shoham et al., on the other hand, require only one inflation tube. In U.S. Pat. No. 5,364,353, there is described a device using a single bladder and an axially expandable bellows with a throttle valve between them. A tube is provided with a lumen for the supply and removal of inflation medium to the bladder and bellows. The throttling valve ensures that the inflation of the bladder is delayed relative to the axial expansion of the bellows as pressure is applied to the inflation tube, and that the deflation of the bladder is delayed relative to an axial contraction of the bellows as pressure is released from the inflation tube, such that the device can be advanced stepwise through, for instance, a gastrointestinal canal.

In PCT Application No. PCT/IL2006/000925, there is described a device having a plurality of inflatable chambers arranged serially, and serially interconnected by means of small orifices, openings or tubes between adjacent chambers, in which at least the first and last chambers are expandable at least radially, and also optionally axially, and other intermediate chambers, if present, are expandable at least axially and also optionally radially. A tube is provided with a lumen for the supply and removal of inflation medium to the chambers. The small orifices, openings or tubes ensure that the inflation of one chamber relative to that preceding it is delayed, such that the chambers inflate sequentially as fluid is pumped into an inflation tube. Likewise, the deflation of a chamber is delayed relative to that in front of it as pressure is released from the inflation tube, such that the device can be advanced stepwise through, for instance, a gastrointestinal canal.

However, in practice, it is found that the control of the inflation and deflation process is critically dependent on the fluid impedance of the small orifices, openings or tubes between the chambers, such that it becomes difficult to obtain such a device which inflates and deflates, and thus, moves, at the desired rate. There thus exists a need for an inflatable balloon device, with a single inflation tube, in which there is good control of the inflation sequence, such that an acceptably high rate of motion over internal passages can be obtained, and without causing undue damage to the inner walls of the passages.

It is to be understood that the terms chamber, balloon, bladder and similar expressions used to describe the inflatable components of the various devices of the present application, may have been used interchangeably and even claimed thuswise, and it is to be understood that no difference is intended to be conveyed by use of one term or the other.

The disclosures of each of the publications mentioned in this section and in other sections of this application, are hereby incorporated by reference, each in its entirety.

SUMMARY OF THE INVENTION

The present invention seeks to provide a new method and device for efficient self-propulsion along internal passageways, of a locomotion device having a series of inflatable chambers in fluid connection by means of passageways between adjacent chambers, and with a single inflation and deflation cycle to propel the device. The device utilizes the dynamic behavior of fluid connected inflated chambers, whereby a time delay in the passage of inflating fluid from rearmost to foremost chamber is utilized to inflate the chambers in sequence beginning with the rearmost, and ending with the foremost. Conversely, this same time delay ensures that deflation of the chambers also proceeds in sequence beginning with the rearmost, and ending with the foremost. The inflatable chambers sequentially grip the inside wall of the passageway, starting with the chamber or chambers disposed at the rear or proximal end of the series while the device expands forward with inflation of the other chambers, and then gripping the inside wall of the passageway with the chamber or chambers situated at the front or distal end of the series, while the device pulls up its rear end with deflation of the other chambers. Instead of being supplied by means of a supply tube, the fluid source can be provided on board, such that the device is able to operate independently of its surroundings.

The device is operable with a series of only two inflatable chambers, each of which expands radially and axially when inflated, but the use of more than two chambers may have an advantage in that the radial pressure on the walls is spread out over more chambers, thus reducing the internal pressure required to anchor the relevant chambers of the device. Furthermore, the use of a larger number of chambers may enable larger payloads to be transported or pulled by the device.

The device differs from prior art devices in that the elastic material of the chambers or balloons and their dimensions are chosen to have a characteristic providing a non-monotonous relationship between the inflation pressure within a chamber and its inflated size. When the material type, skin thickness and balloon dimensions are correctly selected, such a characteristic has an initial pressure peak at a certain initial inflated size, beyond which, as the size of the chamber increases, the internal pressure drops. This means that the elastic properties of the chamber material are such as to allow the volume of the chamber to increases more quickly than the volume inflow of inflating fluid, such that the chamber then continues to grow considerably more rapidly than its rate of growth up to the initial pressure peak. The inflation scenario of the chambers thus acquires a two-part characteristic. During the first stage, the inflation proceeds slowly and monotonously. Consequently, the outflow of fluid into the next chamber in the series is also slow and monotonous. After reaching the initial pressure peak, even for constant fluid inflow, the chamber inflates in size more rapidly, while at the same time, the inflated pressure actually falls. As a result in this fall of internal pressure, the outflow of fluid into the next sequential chamber also falls, while at the same time, the size of the first chamber is increasing more quickly. Ultimately, the expanding chamber inflates to such a size that it meets the lumen wall, anchors there, and can no longer increase in size. From this point of time on, essentially all of the fluid inflow into the chamber flows out into the next sequential chamber, such that it then begins to inflate at the rate provided by the fluid source, and the whole process is repeated for this next chamber.

This combination of events thus enables each chamber in the series to inflate and anchor at a faster rate than the inflation rate of the immediately succeeding chamber. This feature enables the present invention to overcome a possible operative difficulty of prior art, single feed, sequentially inflatable chamber locomotion devices, in that it is difficult to obtain the optimum conditions to combine rapid propulsion speed with sequential inflation of the series of chambers. In such devices, if the orifices between chambers are too small, the inflation rate and propulsion speed are too low. If the orifices between chambers are too large, the chambers inflate so rapidly that there is a tendency for the inflation to approach simultaneous filling conditions, and earlier chambers anchor onto the inside walls of the lumen before they have fully expanded axially, such that the increased inflation rate is not translated into an increased propulsion rate. The use of the non-monotonous elastic material characteristic, according to the present invention, overcomes this possible problem by enabling the use of comparatively large connecting orifices between chambers so that inflation occurs rapidly, but at the same time, introducing a delay in the inflation of the subsequent chambers, such that a subsequent chamber does not inflate significantly until the previous chamber is properly anchored in the lumen. This provides the desired combination of orderly and rapid inflation and anchoring with a high propulsion speed.

The device according to the present invention is particularly useful in medical applications for self-propulsion of a catheter through a lumen, by its tip. It can be applied in various medical fields such as Endoscopy, Gastro-entereology, Urology, Cardiology, Cochlear implantation, sub-dural spinal applications, and others. Although the invention is generally described in this application in terms of its medical application, it is to be understood that the invention is also equally applicable to non-medical applications, where vision, accessibility or maintenance are needed in passageways, such as in industrial plant, gas pipes, power plants, tunnels, utility pipes, and the like.

There is thus provided in accordance with a preferred embodiment of the present invention, a self-propelled device for locomotion through a lumen, comprising:

(i) a set of serially arranged inflatable chambers, adjacent chambers being connected by at least one connecting port providing fluid communication between the adjacent chambers, and (ii) a fluid source attached to an end one of the set of serially arranged inflatable chambers, such that the set of chambers inflate sequentially, (iii) wherein at least one of the inflatable chambers has characteristics providing a non-monotonous relationship between the inflation pressure within the at least one chamber and its inflated size.

In the above described device, the characteristics may comprise at least one of the elastic properties of the elastic material, the wall thickness of the at least one chamber, and the uninflated size of the at least one chamber. The characteristics may also be such that the non-monotonous relationship has an inflation pressure peak at a first inflated size. Additionally, the characteristics may preferably be such that the non-monotonous relationship has a negative slope when the inflated size of the at least one chamber is in a range immediately larger than the first inflated size. Within that range immediately larger than the first inflated size, the volume of the at least one chamber may preferably show an increase more rapidly than the volume of fluid flowing into the at least one chamber, such that the inflation pressure of the at least one chamber falls. Furthermore, the characteristics may be such that the slope of the non-monotonous relationship changes to a positive slope at a second inflated size within the range immediately larger than the first inflated size. The characteristics may be such that at the second inflated size, the inflation pressure goes through a minimum as a function of inflated size.

In accordance with still another preferred embodiment of the present invention, in any of the above described devices, chambers in the set having equal inflation pressures may have different inflated sizes.

There is even further provided in accordance with another preferred embodiment of the present invention, a device as described hereinabove, and wherein the characteristics are such that the at least one inflatable chamber becomes fully inflated before a second chamber adjacent to the at least one inflatable chamber, and distal to the fluid source, has inflated appreciably. In such a case, the at least one inflatable chamber may become fully inflated by virtue of its contact with a wall of the lumen.

In accordance with a further preferred embodiment of the present invention, the device may preferably be adapted for locomotion through a bodily passage of a subject.

There is further provided in accordance with yet another preferred embodiment of the present invention, a method of sequential filling a set of serially arranged inflatable chambers, comprising:

(i) providing a set of serially arranged inflatable chambers, adjacent chambers being connected by at least one connecting port providing fluid communication between the adjacent chambers, and (ii) attaching a fluid source to an end one of the set of serially arranged inflatable chambers, (iii) wherein the characteristics of at least one of the inflatable chambers are selected to provide a non-monotonous relationship between the inflation pressure within the at least one chamber and its inflated size.

In the above described method, the characteristics may comprise at least one of the elastic properties of the elastic material, the wall thickness of the at least one chamber, and the uninflated size of the at least one chamber. The characteristics may also be such that the non-monotonous relationship has an inflation pressure peak at a first inflated size. Additionally, the characteristics may preferably be such that the non-monotonous relationship has a negative slope when the inflated size of the at least one chamber is in a range immediately larger than the first inflated size. Within that range immediately larger than the first inflated size, the volume of the at least one chamber may preferably show an increase more rapidly than the volume of fluid flowing into the at least one chamber, such that the inflation pressure of the at least one chamber falls. Furthermore, the characteristics may be such that the slope of the non-monotonous relationship changes to a positive slope at a second inflated size within the range immediately larger than the first inflated size. The characteristics may be such that at the second inflated size, the inflation pressure goes through a minimum as a function of inflated size.

In accordance with still another preferred embodiment of the present invention, in any of the above described methods, chambers in the set having equal inflation pressures may have different inflated sizes.

There is even further provided in accordance with another preferred embodiment of the present invention, a method as described hereinabove, and wherein the characteristics are such that the at least one inflatable chamber becomes fully inflated before a second chamber adjacent to the at least one inflatable chamber, and distal to the fluid source, has inflated appreciably. In such a case, the at least one inflatable chamber may become fully inflated by virtue of its contact with a wall of the lumen.

In accordance with yet a further preferred embodiment of the present invention, the above described method may further comprise the step of using said set of serially arranged inflatable chambers for providing self-propelled motion through a lumen.

BRIEF DESCRIPTION OF THE DRAWINGS

The present invention will be understood and appreciated more fully from the following detailed description, taken in conjunction with the drawings in which:

FIGS. 3, 4 and 5 are graphs of the pressure inside an inflatable elastic balloon, plotted against the radial expansion of the balloon, for balloons having different elastic inflation characteristics;

DETAILED DESCRIPTION OF PREFERRED EMBODIMENTS

Figure 1:
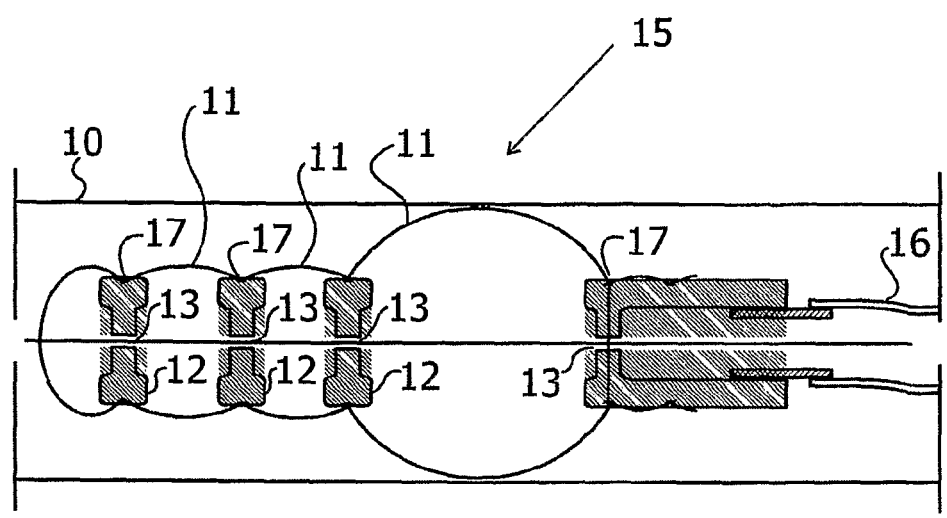
FIG. 1 illustrates schematically a prior art tip-propelled catheter device, such as that described in co-pending PCT Application No. PCT/IL2006/000925.

Reference is now made to FIG. 1, which illustrates schematically a tip-propelled catheter device 15 for traveling down a lumen 10, as is known in the art. The device may preferably comprise a number of balloons 11 connected to each other by separators 12 with one or more small openings, preferably in the form of orifices 13 formed therein, such that all the balloons comprise a single volume, inflatable through a single input. For ease of construction, the device can alternatively and preferably comprise a single inflatable balloon divided into separate balloon segments by separators with orifices such that the entire segmented balloon can be inflated through a single input. The balloon fabric is preferably held in place relative to the separators 12 by means of rings 17 or glued or molded to the separators. Whichever preferred construction is used, the device is connected by a single tube 16 to a fluid supply for inflating the balloons or the balloon segments. For the sake of simplicity, the operation of the device will be explained using the term balloon for each separate segment, although it is to be understood that the invention can equally be implemented using a single balloon segmented to form the separate segments. The inflation fluid used can be any one of a compatible gas or liquid. The fluid supply can alternatively be taken from the passageway through which the device is moving, by means of an on-board pump, and ejected thereto after use.

Figure 2A:
FIGS. 2A, 2B, 2C, 2D, 2E, 2F, 2G, 2H and 2I illustrate schematically how the fluid inflates the balloon cells of a device of the type shown in FIG. 1 in a sequence that causes the device to move forward.
Figure 2B:
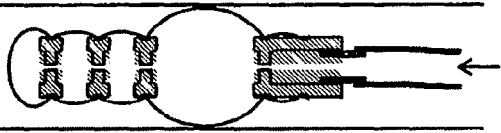
Figure 2C:
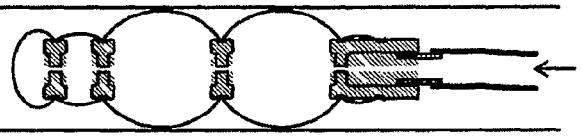
Figure 2D:
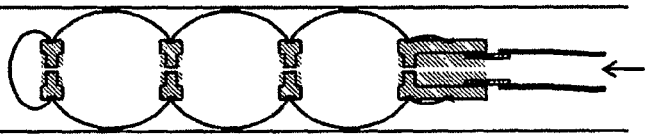
Figure 2E:
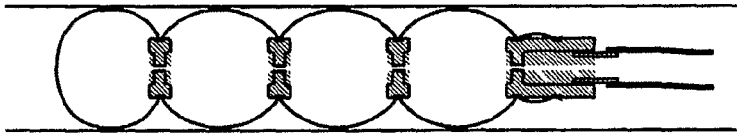
Figure 2F:
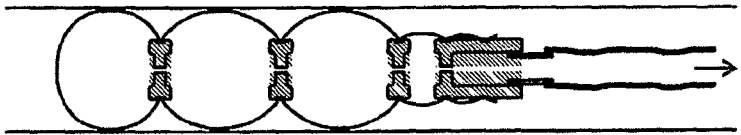
Figure 2G:
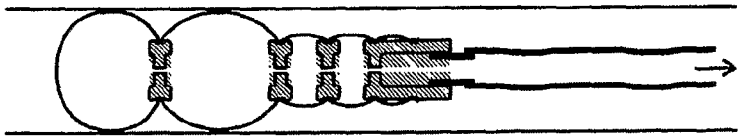
Figure 2H:
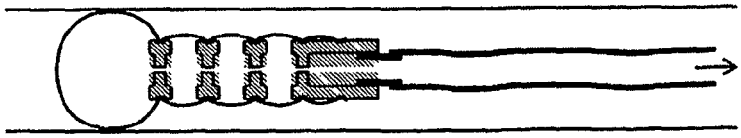
Figure 2I:
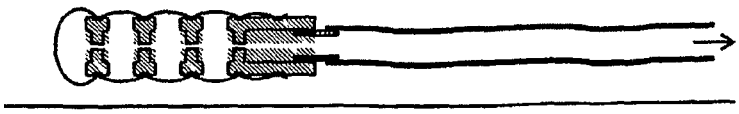

Reference is now made to FIGS. 2A to 2I which illustrates schematically how the fluid inflates the balloon cells in a sequence that causes the proximal one to inflate first, increasing its diameter as well as its length. Being inflated, it locks itself against the inside walls of the tube, but at the same time, its increase in length advances the other cells which are not fully inflated yet and hence are not locked on the inside walls of the tubes. The cells are inflated in a sequence until the distal cell locks against the inner tube walls, but at a position further along the tube than that of the un-inflated balloon distal cell initial position. This situation is reached in FIG. 2E. The timing and order of the sequence is mandated by the fluid flow dynamics through the orifices, and the dynamics of the balloon inflation. Disconnecting the supply and allowing the fluid pressure to drop at this point, or pumping out the fluid, as shown in FIG. 2F, causes the proximal cell to deflate first reducing both its length and diameter. Since the distal cell and all of the intermediary cells, are at this point still fully inflated, they are still locked against the inner walls of the tube, thus pulling the proximal cell inward as the balloon deflates and decreases its length.

The sequential motion series is repeated inducing motion of the entire device as can be seen in FIGS. 2A to 2I. The locomotion sequence is composed of two phases: inflation and deflation, with the arrows at the entrance of the inflation tube indicating the direction of fluid flow. A simplified description of the dynamics of the sequential inflation is as follows:

The flow through an orifice is proportional to the square root of pressure difference across the orifice, and the square of the diameter of the orifice, such that the orifice sizes can be selected to provide specific inflation dynamics.

Inflation phase: Initially, the pressure is equal in each balloon and is equal to the outside pressure, therefore the balloons are in deflated condition, as in FIG. 2A. When the pressure in the supply tube rises, the fluid begins to flow through the first orifice into the first (proximal) balloon, as in FIG. 2B. The pressure difference between the first and second balloons is now lower than the pressure difference between the supply tube and the first balloon, such that the flow rate in the second orifice is slower and the second balloon inflates more slowly than the first one. By this means, the pressure propagates in a gradual manner to the last (distal) balloon until the pressure in all the balloons is equal, as shown in FIG. 2E.

Deflation phase: Now the pressure in the supply tube is reduced to the outside pressure, or the fluid is pumped out of the inflation tube, and there is then a pressure drop between the supply line and the first balloon. The fluid begins to flow out of the first balloon, as in FIG. 2F. Again, since the pressure difference between the supply tube and the first balloon is greater than between the rest of the balloons, the first balloon deflates first, then deflates the second, and so on until the last balloon is deflated, as in FIG. 2I.

In a variation of the actuation sequence, it is possible to initiate the cycling process even before the last cell is fully deflated. In such a case there will always be a base point anchored to the passageway and hence will prevent unwanted slippage in the case of external forces. Different orifices sizes, or different numbers of orifices, can be used between different positioned balloons to improve the locomotion and speed of the device, all according to the dynamics of the fluid flow in to, out of, and between balloons. Furthermore, the viscosity of the inflation fluid can be chosen to improve the locomotion dynamics.

As previously stated, the time delay between sequential inflation of the balloons is dependent primarily on the fluid impedance of the orifice connecting neighboring balloons. However, it has been found in such a device, that in spite of the apparent simplicity of the temporal control of the inflation time delay between successive balloons, it is difficult to control the fluid flow to obtain acceptable performance of the device. If the orifices are too small, the whole inflation procedure takes too long and the propulsion speed of the device is slow. If the orifices are too large, the pressure drop between neighboring balloons is small, and since the radii of successive balloons is, for an elastic material having a monotonous relationship between the internal pressure and inflation size, proportional to their inflation pressure, at any point of time during the inflation and deflation process, there is little difference in diameter between successive balloons. Therefore, although successive balloons do inflate sequentially, the inflation sequence becomes so fast that it approaches simultaneous inflation, and is difficult to regulate. The same is applicable to the deflation process. Such a rapid inflation sequence may be disadvantageous in some applications, because friction with the lumen wall of the rapidly expanding balloons may impede the axial expansion of the successive balloons, and thus reduce the propulsion speed of the device. This problem may be of great importance in such common applications as passage through the gastro-intestinal tract, where the tendency of the internal wall of the tract to contract elastically means that it will generally be in contact with the balloons as they inflate both radially and axially. With such prior art devices, there is therefore a trade-off between the speed of inflation of the successive balloons, by which maximum inflation speed would have been expected to result in optimum propulsion speed of the device along the lumen, and the actually achieved propulsion speed, these factors sometimes working against each other. It would therefore be desirable that, without reducing propulsion speed, successive non-anchoring balloons should delay their inflation time until only a short time before anchoring, such that their friction with the lumen wall remains low until a moment before anchoring. Such an arrangement would provide optimum propulsion speed along the lumen, since the inflation sequence would then more resemble a step sequence of inflation, rather than a close-to-continuous and almost simultaneous inflation. The object would thus be to provide a method of slowing down successive balloon inflation without appreciably slowing down the whole inflation sequence by restricting the orifice flow rate.

The above described performance of a serial set of inflating balloons arises because of the use of balloons made of an elastic material and having dimensions such that they have a monotonous dependence of inflation size with internal pressure. According to a preferred embodiment of the present invention, there is proposed a method of constructing the balloons of a serial set of inflatable balloons, which enables the generation of such a desired delay in the inflation of sequential balloons, such that the problem of almost simultaneous inflation can be solved, but without substantially reducing the propulsion speed of the device. The novel construction is based on selection of the elastic properties of the balloon material, the size of the balloons and the balloon wall thickness, such that the balloons have a non-monotonous inflation characteristic with pressure.

Thus, for example, the well-known phenomenon that the pressure required to inflate a latex rubber party balloon is higher in the early stages of inflation, than when the balloon is already partly inflated, is due, at least in part, to such a non-monotonous characteristic of the balloon. (Additionally, part of the increasing ease of inflation is due to the breaking of some of the monomer chains in the polymer during the first inflation.) The behavior of inflated balloons has been described in the book "Rubber and Rubber Balloons: Paradigms of Thermodynamics" by I. Müller and P. Strehlow, published as a volume in Lect. Notes. Phys., Vol. 637, (2004) by Springer Verlag, Berlin. In chapters 2 and 3 thereof, pages 7 to 34, herein incorporated by reference in their entirety, there is shown, inter alia, the derivation of the relationship between the inflation pressure of a balloon and its size, which is given on page 28, for a spherical balloon, by the formula:

$$[p] = 2s + \frac{d_0}{r_0}\left(\frac{r_0}{r} - \left(\frac{r_0}{r}\right)^7\right)\left(1 - \frac{s_-}{s_+}\left(\frac{r}{r_0}\right)^2\right) \quad (1)$$

Where:
p is the inflation pressure of the balloon;
$s_+$ and $s_-$ are elastic constants of the balloon material, which are dependent on the mass density of the material, the molecular mass of the polymer chain making up the elastic material of the balloon (about 120 isoprene molecules in the case of rubber), and the temperature, as fully derived on pages 32 to 34 of the Muller book;
$d_0$ is the wall thickness of the balloon;
$r_0$ is the uninflated balloon radius; and
r is the radius of the inflated balloon at pressure p.

Reference is now made to FIGS. 3 to 5, which show the pressure, measured in atmospheres, inside an inflatable spherical elastic balloon, plotted against the radial expansion of the balloon, expressed as the ratio of its inflated to its uninflated radius, $r/r_0$. The graphs are derived using equation (1), for a specific type of rubber, and each graph is plotted for a different value of the elastic parameter $s_-$. FIG. 3 shows the characteristic curve for $s_-=-0.3$ bar, FIG. 4 for $s_-=-0.5$ bar, and FIG. 5 for $s_-=-0.8$ bar. As is observed, the behavior of the balloon during inflation is dependent on the balloon material parameters, as well as on the wall thickness, the balloon radius, and even on the shape of the balloon, since the calculations for equation (1) are applicable only for spherical balloons. FIG. 3 shows marked non-monotonous elastic behavior, FIG. 4 shows very mild non-monotonous behavior, while the conditions of FIG. 5 show monotonous behavior.

According to a preferred embodiment of the present invention, the balloon material is selected, and the balloon dimensions and shape are chosen such that the balloons have a non-monotonous pressure/radius characteristic, such as that shown in FIG. 3. Looking at the practical consequences of the inflation curve of FIG. 3, an initial inflation pressure is required to inflate the balloon to a certain inflation point, defined in this application as the initial inflation peak, designated 30 in FIG. 3. From that point onwards, there is a further inflation region with a negative inflation pressure coefficient, such that the balloon continues to inflate even though the pressure is reduced. In order to clarify this feature, it is to be emphasized that this is not meant to imply that the balloon will continue to inflate even if no inflation fluid is added, but rather that for a given inflow of inflating fluid, the volume of the balloon will increase more rapidly than the volume of fluid inflow, such that the internal pressure drops. This negative coefficient region persists as balloon radius increases, until a point of inflation is reached where the inflation pressure required to increase the radius reaches a local minimum, 31, defined in this application as the intermediate inflation pressure minimum. Further increase in inflated radius is only then achieved with an increase of pressure. An internal pressure as high as the original initial inflation peak, is only achieved during the continued inflation of the balloon after a further increased inflation radius is reached, this being shown at point 32 in FIG. 3.

As a result of this behavior, there is a region of the inflation envelope of the balloon, defined as that where the balloon has an internal pressure between the initial inflation peak 30 and the intermediate inflation pressure minimum 31, in which there is no unique value of balloon radius related to a predetermined inflation pressure. Thus, in the preferred example shown in FIG. 3, at a predetermined fixed pressure of, for example, 1.033 bar, there are three possible balloon inflation radii which can co-exist, at approximate values of $r/r_0=1.25$, 2.1 and 4.7, the radius actually achieved being dependent on the history of the inflation procedure. Thus, for a series of connected balloons having the same internal pressure, different balloons can have widely different radii. This phenomenon is used in this embodiment of the present invention to enhance the behavior of the device by allowing successive balloons to have smaller radii than the previously inflated balloons for a longer period than that obtained with monotonous elastic materials, until pressure equilibrium is obtained. This is in contrast to the case of balloons having monotonous inflation characteristics, such as is shown in FIG. 5, according to which balloons having the same or similar internal pressures will all have similar radii, such that large orifices associated with high speed inflation would also have small pressure drops between balloons, and therefore similar internal pressures and hence similar inflation ratios.

Figure 6A:
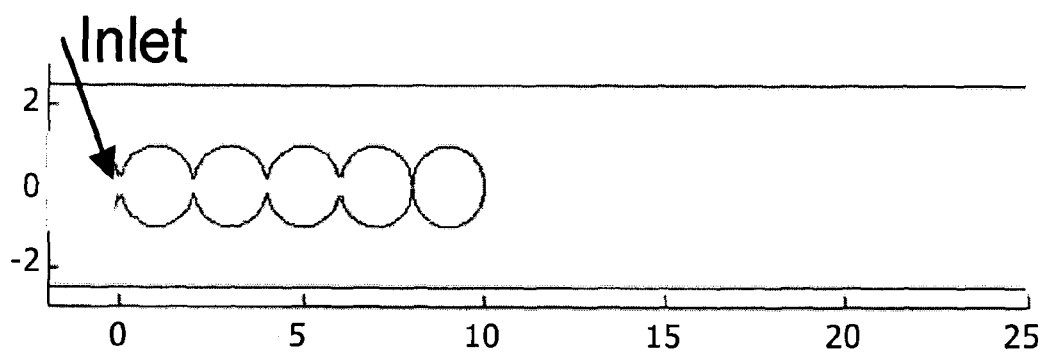
FIGS. 6A and 6B illustrate schematically a locomotion device according to a preferred embodiment of the present invention, comprising a series of inflatable balloons constructed of elastic material having the characteristics shown in the graph of FIG. 3.
Figure 6B:
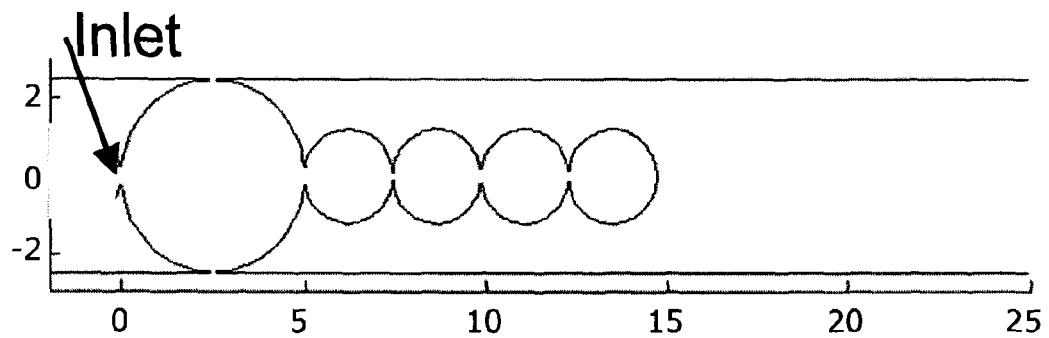

Reference is now made to FIGS. 6A and 6B, which are schematic illustrations of a series of connected balloons, similar in structure to those shown in FIG. 1 and FIGS. 2A-2I of this application, but wherein the balloon material has elastic properties such that the inflation curve as a function of pressure has a non-monotonous form, such as is shown in FIG. 3. The balloon sizes are taken directly from computer simulations of the device. It is seen that in FIG. 6B, where the first balloon has been just fully inflated, the other balloons are all only about 1.2 times their initial radius, thus illustrating how the inflation process of the present invention operates as required.

If the fluid pumping rate into the first balloon, less the fluid outflow rate through the orifice to the following balloons, is such that the inflation pressure in the first balloon only reaches a pressure well below the initial inflation peak, the balloon will not inflate sufficiently to perform its function well. This function is characterized by the need for the device to have sufficient radial space for a useful sized payload, and yet still to be slim enough when uninflated to enable easy insertion into the lumen to be negotiated. This means that in practical terms, the ratio of the fully inflated radius, r, to the uninflated radius, $r_0$, should preferably be at least 1.5, and more preferably, at least 2.

In terms of the exemplary material and dimensions shown in the embodiment of FIG. 3, the fluid inflow rate relative to the fluid outflow rate through the orifice should be such as to ensure that the pressure in the first balloon reaches the initial inflation peak 30. Up to this point, the first balloon grows at a rate determined by the net inflow of fluid. However, as soon as the pressure in the first balloon reaches the initial inflation peak, 30, the balloon will continue growing rapidly from a small net inflow of fluid, even though the pressure now falls down below the initial inflation peak because of the rapid growth. The outflow of fluid into the second balloon does not yet result in the second balloon reaching initial inflation peak, and the second balloon therefore inflates significantly more slowly than the first. Furthermore, the fall in pressure in the first balloon beyond the initial inflation peak reduces the inflow of fluid into the second balloon. At some point within this range beyond the initial inflation peak, the first balloon will anchor onto the walls of the lumen, will cease expanding, and then all of the additional inflowing fluid will pass through the orifice to inflate the second balloon. Here, the process will be repeated again, with the second balloon expanding at its slow rate until its initial inflation peak point has been reached, and then at a faster rate until it anchors in the lumen. As a consequence of this action, even with a comparatively large orifice size to ensure a sufficiently fast inflation cycle time for the entire series, the non-monotonous elastic properties of the balloon material cause the second balloon to refrain from filling significantly until the first balloon is fully inflated and anchored in the lumen. Therefore, in contrast to the continuous inflation process obtained using monotonously elastic materials, which, when the orifice is large enough, acquires an almost simultaneous character, when using the non-monotonous elastic material construction of the present invention, the inflation process acquires a pulse-like inflation sequence, each balloon inflating in a temporally distinct operation, which is desirable for ensuring unfettered progress of the device through the lumen. The same sequence of events operates in reverse when deflation is taking place.

Figure 7:
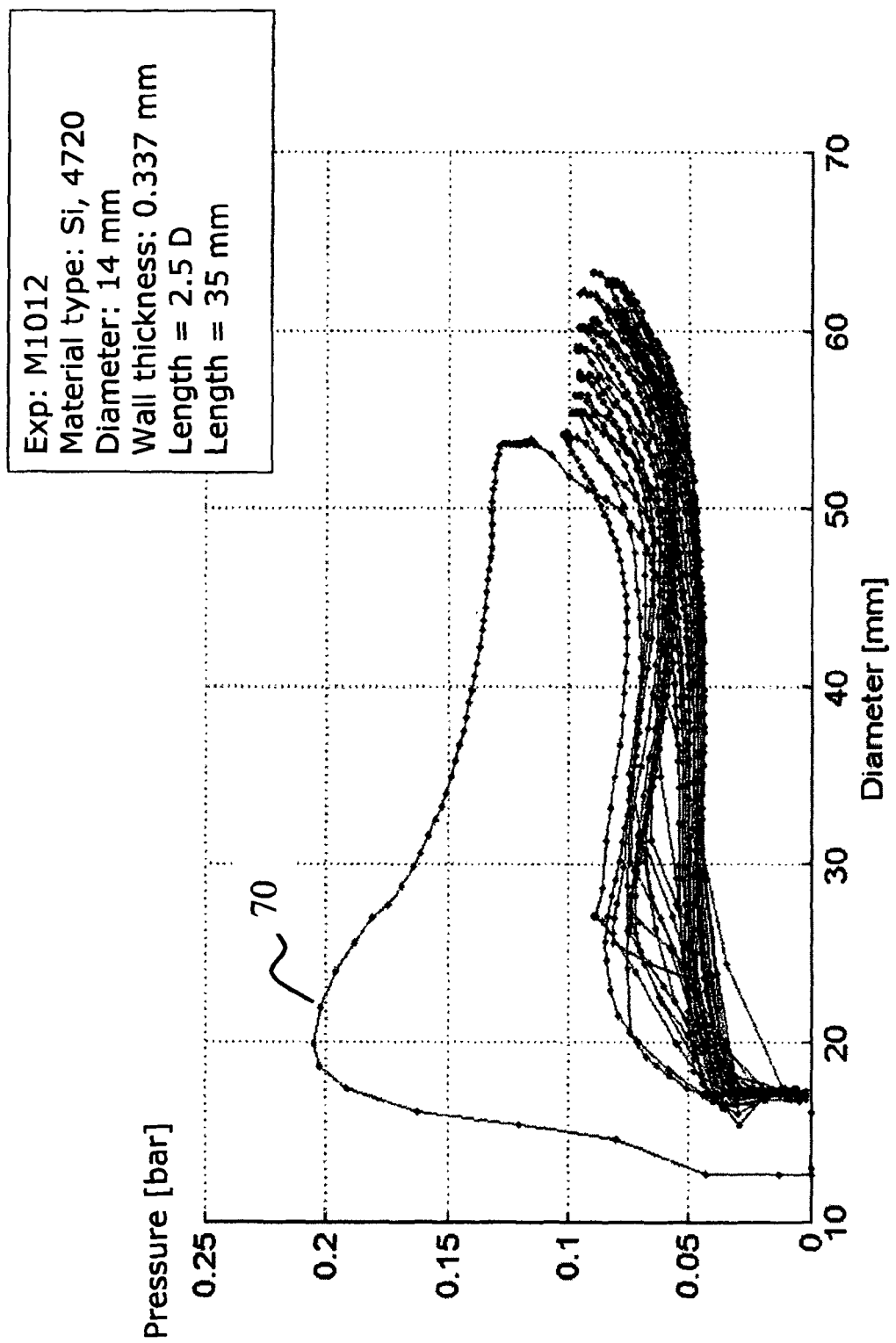
FIGS. 7 and 8 illustrate examples of inflation characteristics, experimentally determined to obtain the desired properties and dimensions of a set of inflatable balloons for use in a device for navigating the colon of a subject.
Figure 8:
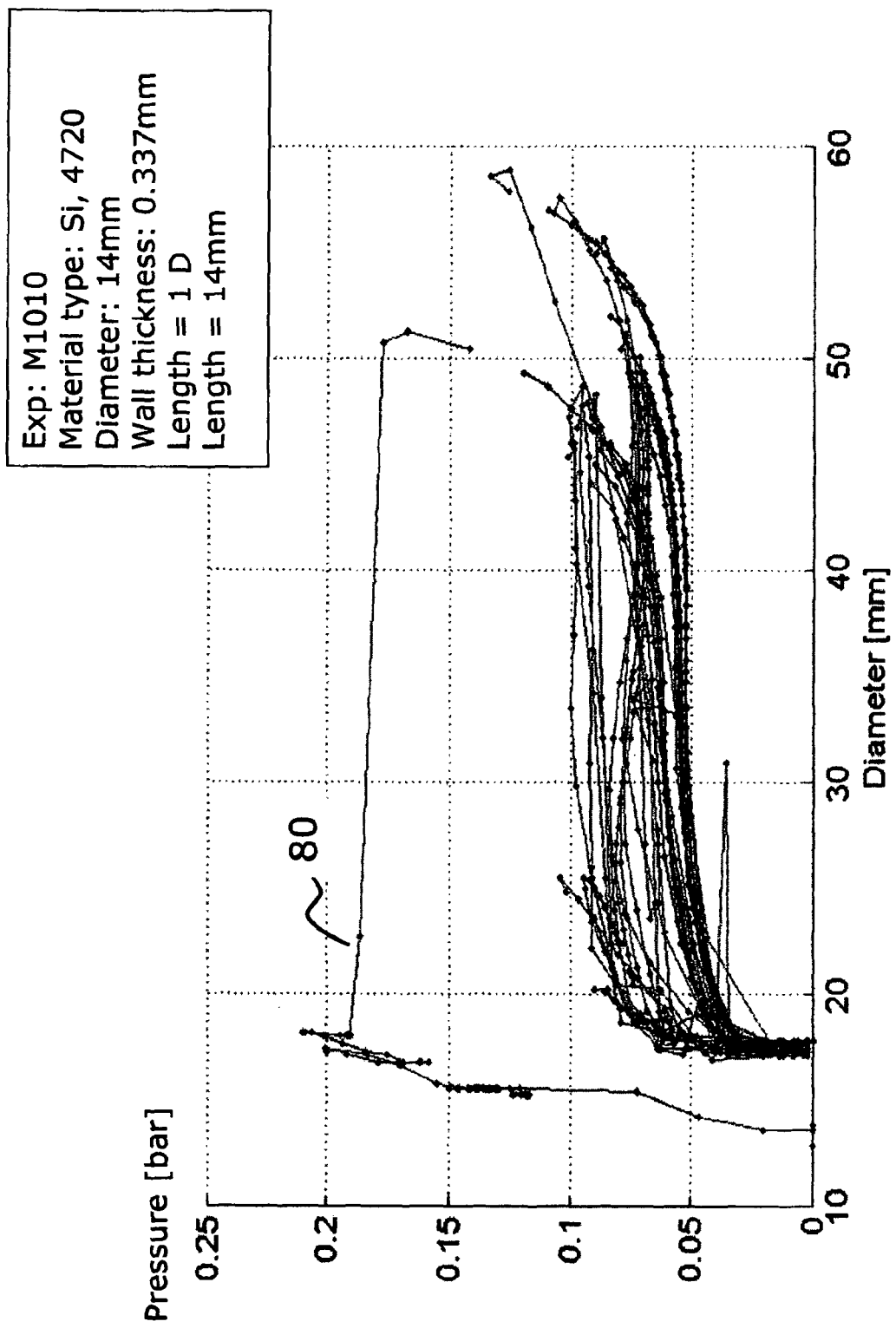

Reference is now made to FIGS. 7 and 8 which illustrate two examples of inflation characteristics, experimentally determined in order to obtain the desired properties and dimensions of a set of inflatable balloons for use in a device for navigating the colon of a subject. The graphs were plotted by repeatedly inflating and deflating the balloon, and plotting diameter as a function of inflation pressure. The first inflation path, 70 in FIG. 7, and 80 in FIG. 8, is markedly different from the subsequent curves, and is not taken into account in the experimental assessment of balloon characteristic suitability. The balloons are preferably not spherical but cylindrical, having a larger length than their diameter, such that they have a longer axial expansion when inflated. The device then moves further during each cycle, than a device using spherical balloons of similar characteristics. In the embodiment whose results are shown in the graph of FIG. 7, the length of the balloon is 2.5 times the diameter, the diameter being 14 mm and the length 35 mm. The balloon material is a silicone, type 4720, of thickness 0.337 mm. Although there is a spread of the experimental results, the non-monotonous nature of the inflation characteristic is clearly seen, making this balloon a good candidate for a device which will move efficiently and speedily. Furthermore, for use in the colon, since an initial inflation peak of less than 100 mBar is desired, to prevent the possibility of pressure injury to the colon, the sample shown in FIG. 7 complies with this requirement. It is found that the deflation curve is slightly different from that of the inflation, as shown by the lower groups of lines in each graph.

In the example of FIG. 8, the balloon is made of the same material and the same thickness as that of FIG. 7, but is essentially spherical, having a diameter of 14 mm. As is seen from FIG. 8, the inflation is almost monotonous, such that this balloon, although made of identical material of the same thickness as in FIG. 7, is not suitable for use in a speedy and efficient device.

The various parameters of the balloons are varied in order to achieve the best non-monotonous result, within the limitations of the maximum pressure that can be applied to the balloon, this being dependent on the application in hand. Because of the complexity of the analytical form of the balloon inflation characteristics, as shown by equation (1) above, the experimental method outlined here is generally the simplest method for targeting the balloon properties required for each application.

In implementing the invention for different applications, various parameters have to be taken into account in order to devise the most suitable device for the application. Thus, for use in the gastro-intestinal tract, the following general guidelines appear to be useful:
Max.Pressure: 30-100 mBar. Use of inflation pressures above this range in a self-propelled device in the colon may cause injury, since the colon contracts onto any body within itself, and thus all of the pressure within the balloons is transferred directly to the colon wall.
Diameter: 8-20 mm
Balloon length: 10-50 mm, to provide good axial stroke.

In other body passages, the pressure range will be similar but the diameter may change according to the passage diameter.

It is to be understood that these exemplary embodiments and their experimental results are not meant to limit the invention in any way, but are brought only as exemplary embodiments of how the invention maybe implemented in some common medical applications. The device may also be used for remote access in industrial pipelines which it is required to traverse. For such industrial applications, there will generally be no critical limitations about the maximum balloon pressure allowable, and even more efficient and speedy devices may be designed than for medical application.

It is appreciated by persons skilled in the art that the present invention is not limited by what has been particularly shown and described hereinabove. Rather the scope of the present invention includes both combinations and sub-combinations of various features described hereinabove as well as variations and modifications thereto which would occur to a person of skill in the art upon reading the above description and which are not in the prior art.

We claim:

1. A self-propelled device for locomotion through a lumen, comprising:
 a set of serially arranged inflatable chambers, adjacent chambers being connected by at least one connecting port providing fluid communication between said adjacent chambers; and
 a fluid source attached to an end chamber of said set of serially arranged inflatable chambers,
 wherein said set of chambers is configured such that flow of fluid from said fluid source inflates the chambers of said set of chambers in a sequence beginning with said end chamber, said sequential inflation resulting in locomotion of said set of chambers through said lumen, and
 wherein at least one chamber of said set of inflatable chambers comprises characteristics selected to provide a non-monotonous relationship between the inflation pressure within said at least one chamber and its inflated size.

2. A self-propelled device according to claim 1, wherein said characteristics include the elastic properties of the material of said at least one chamber, the wall thickness of said at least one chamber, and the uninflated size of said at least one chamber.

3. A self-propelled device according to claim 1, wherein said characteristics are such that said non-monotonous relationship has an inflation pressure peak at a first inflated size.

4. A self-propelled device according to claim 3, wherein said characteristics are such that said non-monotonous relationship has a negative slope when the inflated size of said at least one chamber is in a range immediately larger than said first inflated size.

5. A self-propelled device according to claim 3, wherein said characteristics are such that within said range immediately larger than said first inflated size, the volume of said at least one chamber increases more rapidly than the volume of fluid flowing into said at least one chamber, such that the inflation pressure of said at least one chamber falls.

6. A self-propelled device according to claim 3, wherein said characteristics are such that the slope of said non-monotonous relationship changes to a positive slope at a second inflated size within said range immediately larger than said first inflated size.

7. A self-propelled device according to claim 6, wherein said characteristics are such that at said second inflated size, said inflation pressure goes through a minimum as a function of inflated size.

8. A self-propelled device according to claim 1, wherein chambers in said set having equal inflation pressures can have different inflated sizes.

9. A self-propelled device according to claim 1, wherein said characteristics are such that said at least one inflatable chamber becomes fully inflated before a second chamber adjacent to said at least one inflatable chamber, and distal to said fluid source, has inflated appreciably.

10. A self-propelled device according to claim 9, wherein said at least one inflatable chamber becomes fully inflated upon its anchoring on a wall of said lumen.

* * * * *